United States Patent [19]

Cramer et al.

[11] Patent Number: 5,225,542

[45] Date of Patent: Jul. 6, 1993

[54] SPECIFIC CARBOHYDRATE-BINDING PROTEINS (LECTINS) OF MAMMALIAN TUMOR CELLS

[75] Inventors: Friedrich Cramer; Hans-Joachim Gabius, both of Goettingen, Fed. Rep. of Germany

[73] Assignee: Max-Planck Gesellschaft zur Foerderung der Wissenschaften e.V., Goettingen, Fed. Rep. of Germany

[21] Appl. No.: 641,335

[22] Filed: Jan. 15, 1991

Related U.S. Application Data

[63] Continuation of Ser. No. 881,050, Aug. 22, 1986, abandoned.

[30] Foreign Application Priority Data

Oct. 23, 1984 [DE] Fed. Rep. of Germany ..... 84112759

[51] Int. Cl.$^5$ ............ A61K 39/395; C07K 15/06; C12P 21/00; G01N 33/574
[52] U.S. Cl. ............................................ 530/396
[58] Field of Search ............................ 530/395, 396

[56] References Cited

PUBLICATIONS

Gabius, Hoppe-Seyler's Z. Physiol. Chem. Bd. 365, 5.633–638, Jun. 1984 (English language translation).

*Primary Examiner*—Ronald W. Griffin
*Attorney, Agent, or Firm*—Kenyon & Kenyon

[57] ABSTRACT

Carbohydrate-binding proteins (lectins) of mammalian tumor cells and processes for their preparation. These lectins, the corresponding carbohydrates and the corresponding monoclonal antibodies are suitable for rapid, reliable and precise differential diagnosis of tumors and for the product of pharmaceutical compositions for the treatment of tumors.

29 Claims, 2 Drawing Sheets

HETEROTYPIC AGGREGATION

HOMOTYPIC AGGREGATION

SPECIFIC CARBOHYDRATE-BINDING PROTEINS (LECTINS) OF MAMMALIAN TUMOR CELLS

This application is a continuation of application Ser. No. 06/881,050, filed Aug. 22, 1986, now abandoned.

TECHNICAL FIELD OF THE INVENTION

This invention relates to carbohydrate-binding proteins (lectins) of mammalian tumor cells which specifically recognize and bind to carbohydrate molecules and to methods of isolating these lectins from mammalian tumor cells.

BACKGROUND ART

The designation "lectin" is derived from the property of certain proteins to "select" (i.e. recognize) specific carbohydrate structures and to form a lectin-carbohydrate complex.

Lectins can be defined as follows:
the recognition of carbohydrates is highly specific and thus comparable to the antigen-specificity of antibodies or the substrate-specificity of enzymes;
in contrast to antibodies which can also specifically recognize carbohydrate-residues of glycoconjugates, lectins are of non-immune origin;
in contrast to enzymes which can also specifically recognize carbohydrates or glycoconjugates, lectins do not display any detectable enzymatic activity;
they display carbohydrate-inhibitable homotypic and heterotypic agglutinating activity (see FIG. 1), e.g. of bacteria or blood cells as trypsinized and glutaraldehyde treated rabbit erythrocytes.

From this definition of lectins it can be taken that for the clear identification of a protein as a lectin, the properties of the protein have to fulfil all the above-mentioned prerequisites. Otherwise the protein in question could, for instance, also be an antibody or an enzyme.

The binding of lectins to their corresponding carbohydrates can be either $Ca^{2+}$-dependent or $Ca^{2+}$-independent, i.e. some of the lectins form a complex with the respective carbohydrate only in the presence of $Ca^{2+}$-ions.

Until very recently lectins were thought to be peculiarities of the plant kingdom. The physiological role of these proteins is still not known. During the last few years it has become apparent that lectins are regular components of almost every cell membrane or cell surface. Although not much is known yet in this field of research, it is suggested that lectins play a key role in many intercellular processes together with the corresponding carbohydrates on other cells. They form what is probably the most important cellular recognition and communication system and might be important in the development of organs, especially in the development of the central nervous system. Furthermore, they are believed to play a role in fertilization (when sperm and egg recognize each other) and are important in endocytosis; see Barondes, Ann. Rev. Biochem. 50 (1981), p. 207.

Gabius et al. (Hoppe-Seyler's Z. Physiol. Chem. 355 (1984), p. 633), describe $Ca^{2+}$-independent lectins which were isolated from bovine pancreas and have a molecular weight of 16,000, 35,000 and 64,000, respectively. They bind specifically the $\beta$-galactosides lactose and asialofetuin and the $\alpha$-galactoside melibiose. Furthermore, fucose-binding lectins which are $Ca^{2+}$-dependent and have a molecular weight of 34,000; 62,000; and 70,000; respectively, are described.

Ashwell et al. (Ann. Rev. Biochem. 51 (1982), p. 531) describe $\beta$-galactoside-specific receptors of the liver which specifically recognize asialo-glycoside residues of proteins and are responsible for the uptake of these glycoproteins into hepatocytes. Furthermore, a hepatic mannan-specific receptor is described. J. Biochem. 94 (1983), p. 937 data of a protein with $Ca^{2+}$-dependent mannan-binding specificty. The protein was isolated from the mesenteric lymph nodes of rats and from human serum. It was, however, not analyzed according to the parameters given above, whether this protein actually is a lectin.

Rutherford et al. (FEBS Lett. 136 (1981), p. 105) describe the isolation and characterization of a mannan-binding lectin of the vitelline membrane of the early chick embryo. The physiological role of this protein, however, is not disclosed.

From a publication of Roberson and Barondes (J. Biol. Chem. 257 (1982), p. 7520) a lectin of Xenopus laevis oocytes, X. laevis embryos and the liver of the adult X. laevis is known. The lectin under investigation displays different specific activities in the three different differentiation stages.

Grabel et al. (Cell 17 (1979), p. 477) published the occurrence of a carbohydrate-binding component on the surface of teratocarcinoma stem cells. This component is designated by the authors as a lectin-like component and not as a lectin. Thus, this reference does not disclose whether or not the carbohydrate-binding component found is a lectin.

Moreover, this publication does not contain any characterizing data concerning the carbohydrate-binding component. What is disclosed there is just an observation on the association of cells, which can be inhibited by the addition of mannose-rich glycoproteins as yeast invertase, yeast, mannans and horse radish peroxidase. A further publication of Grabel et al. (Biophys., Biochem. Res. Comm. 102 (1981), p. 1165) refers to the extraction of mouse teratocarcinoma cells. According to the authors, this extract contains a fucoidan-inhibitable hemagglutination activity.

In the papers of Raz et al. (Cancer Res. 41 (1981), p. 3642), Roche et al. (J. Cell. Biochem. 22 (1983), p. 131) and Teichberg et al. (Proc. Natl. Acad. Sci. U.S.A. 72 (1975), p. 1383) a $\beta$-galactoside specific hemagglutination activity, a glucose-specific endocytosis activity, and a $\beta$-galactoside-specific hemagglutination activity, respectively, are described which were detected on the surface of tumor cells or in the extracts of tumor cells. It has to be understood, however, that the papers of Grabel et al. (supra), Raz et al. (supra), Roche et al. (supra), and Teichberg et al. (supra) do not show the presence of lectins on the surface or in the cytoplasm of tumor cells. The presence of lectins is only proved if all of the above-mentioned parameters characterizing a protein as a lectin are investigated. If such a complete characterization is not carried out, the carbohydrate-specific protein may also be an enzyme of the cellular carbohydrate and glycoconjugate metabolism, see e.g. Roseman (Chem. Phys. Lipids 5 (1970), p. 270). In this publication of Roseman, the occurrence of glycosyltransferases as cell surface-exposed carbohydrate-specific proteins has been suggested. This hypothesis was confirmed by e.g. Rauvala et al. (Proc. Natl. Acad. Sci. U.S.A. 80 (1983), p. 3991).

Finally, lectins were identified in chicken liver and embryonic chicken muscle (Ceri et al., J. Biol. Chem. 256 (1981), p. 390; de Waard et al., J. Biol. Chem. 252 (1976), p. 5781), human lung (J. T. Powell, Biochem. J. 187 (1980), p. 123) and human liver (Wild et al., Biochem. J. 210 (1983), p. 167).

Thus, lectins of mammalian tumor cells have not been characterized.

BRIEF SUMMARY OF THE INVENTION

One object of the present invention therefore is the provision of specific carbohydrate-binding proteins (lectins) which are obtained from a mammalian tumor cell.

A further object of the present invention is the provision of specific carbohydrate-binding proteins (lectins) which are obtained from a mammalian tumor cell and which are responsible for specific surface properties of said tumor cell.

Still further, it is an object of this invention to provide a process for obtaining lectins from mammalian tumor cells which are responsible for specific surface properties.

In the process of the present invention the tumor tissue is first extracted with acetone, precipitating the protein and thus separating it from e.g. lipids. The acetone from the precipitate is then evaporated to obtain an acetone powder. The acetone powder is extracted with a suitable buffered aqueous solution in order to solubilize the lectin(s). Then the resulting aqueous extract is subjected to at least one affinity chromatography using columns to which carbohydrates which can be recognized by lectins are bound. Typical examples of such carbohydrates are lactose, asialofetuin, melibiose, mannan, fucose, invertase and heparin. Lactose and asialofetuin are classified as $\beta$-galactosides, melibiose as an $\alpha$-galactoside. In this chromatography, lectins which are specifically recognizing the carbohydrate bound to the column will bind themselves to said columns. Subsequently these lectins are eluted from the column using an aqueous solution of the respective carbohydrate having e.g. a concentration of 0.3 or 0.5M. Finally, the lectins are investigated with respect to their molecular weight and to their properties in hemagglutination-, enzyme activity-and aggregation-assays.

Essentially according to this method lectins of a rat rhabdomyosarcoma, a rat fibroadenoma, a rat invasive tubulopapillary adenocarcinoma with a low degree of differentiation, a rat non-invasive tubulopapillary adenocarcinoma with a high degree of differentiation, a murine teratoma, a human malignant epithelial tumor, a human teratocarcinoma (H12.1), a human embryonic carcinoma (H23), a human yolk sac carcinoma, a rat osteosarcoma, and a human sarcoma (Ewing's sarcoma) were isolated and characterized.

The lectins of the present invention can be used to provide corresponding monoclonal antibodies and subfragments thereof. Monoclonal antibodies, e.g. mouse or human antibodies, are isolated from suitable producer cells, e.g. hybridoma cell lines, according to known methods.

Anti-lectin-antibody-subfragments, such as the Fab and F(ab'$_2$) fragments can be prepared by proteolytic cleavage of the antibody molecule with the enzymes papain and pepsin, respectively, followed by purification.

The monoclonal anti-lectin-antibodies, or their subfragments, or lectins, or carbohydrates which are recognizable by said lectins can be conjugated with a chemotherapeutic or biologically active compound (such as 5-fluoruridine, vincristine, daunomycine or methothrexate), with a fluorescent or radioactively labelled group, or with another compound permitting the detection of said molecules of monoclonal anti-lectin-antibodies or their subfragments, or lectins, or carbohydrates which are recognizable by said lectins in a suitable assay for differential diagnosis of tumor types and the developmental stage of tumors.

Finally, the molecules referred to above can be used to provide diagnostic and pharmaceutical compositions, useful for rapid, reliable and precise clinical diagnosis, for scientific research, and for highly specific tumor therapy and inhibition of metastasis in mammalians and preferentially in humans. The pharmaceutical compositions containing at least one type of said carbohydrates are applicable also in a state of neoplastic disease, where the risk of metastasis is strongly increased, e.g. after surgical treatment.

The molecules referred to above can be utilized in a composition such as tablet, capsule, solution or suspension. They may be compounded in a conventional manner with a physiologically acceptable vehicle or carrier, excipient, binder, preservative, stabilizer, flavor, etc. as called for by accepted pharmaceutical practice.

DETAILED DESCRIPTION OF THE INVENTION

In a first embodiment of the present invention five tumor types were investigated biochemically for the presence and characteristics of endogenous lectins.

A rat rhabdomyosarcoma revealed only $Ca^{2+}$-independent-lectin-specificities.

A rat fibroadenoma of the mammary gland was also investigated. It contained a diverse pattern of lectins.

The lectin pattern of a spontenaous invasive rat tubulopapillary adenocarcinoma of the mammary gland was also diverse.

Additionally, a spontaneously occurring non-invasive raT tubulopapillary adenocarcinoma of the mammary gland was analyzed.

The tubulopapillary adenocarcinomas differed in their degree of differentiation and malignancy; the first one had a lower degree of differentiation. Since fibroadenoma and tubulopapillary adenocarcinoma of the rat mammary gland are morphologically similar to their counterparts in humans, these studies on the pattern of carbohydrate-binding lectins also have significance for human breast cancer.

Extracts using 0.2M NaCl (salt) and 2% Triton ®X-100 (detergent) from a murine teratoma contained at least nine different lectins.

Furthermore, according to the present invention the pattern of different endogenous lectins of a human malignant epithelial tumor was investigated.

Additionally, according to the present invention three human testicular tumors were analyzed, namely a human teratocarcinoma (H12.1), a human embryonic carcinoma (H23), and a human yolk sac carcinoma.

Furthermore, the lectin pattern of two sarcomas was analyzed, namely of a rat osteosarcoma and of a human sarcoma (Ewings's sarcoma).

The lectins of the present invention which were isolated from said tumors and which were not known from any normal mammalian tissue are summarized in Table I.

TABLE I

| | Endogenous tumor-derived lectins of the present invention | | | | | | | | | |
|---|---|---|---|---|---|---|---|---|---|---|
| | $Ca^{2+}$-dependent | | | | | $Ca^{2+}$-independent | | | | |
| Tumor type | Lactose | Asialofetuin | Melibiose | Mannan | Fucose | Lactose | Asialofetuin | Melibiose | Mannan | Fucose |
| Rat rhabdomyosarcoma | — | — | — | — | — | — | — | 29<br>43<br>45 | 60–72 | 60–72 |
| Rat fibroadenoma | 52<br>67<br>130 | 52<br>67<br>130 | 52<br>67<br>74 | 52<br>67 | 29<br>67 | — | — | — | — | — |
| Rat invasive tubulopapillary adenocarcinoma (low degree of differentiation) | 32<br>64 | — | — | — | 140 | 22<br>52 | n.d. | n.d. | 44<br>46 | 13<br>30<br>42<br>45<br>62 |
| Rat non-invasive tubulopapillary adenocarcinoma (high degree of differentiation) | — | — | —<br>— | — | 29<br>35 | — | — | 29<br>50<br>52 | — | 29<br>31<br>50<br>52 |
| Murine teratoma | 24 | — | — | 32 | 32 | — | — | — | — | ~100 |
| Human malignant epithelial tumor | 70 | — | 28<br>43<br>45 | — | 62<br>70 | — | — | 64 | — | 62 |
| Human teratocarcinoma (H12.1) | — | — | 31 | — | 31<br>70 | — | — | — | 68 | — |
| Human embryonic carcinoma (H23) | — | — | 56<br>66 | 66 | 31 | 32 | — | — | — | — |
| Human yolk sac carcinoma | 56 | — | 56 | — | 29<br>56 | 29<br>56 | 29<br>56 | 29<br>56 | — | 29<br>56<br>62 |
| Rat osteosarcoma | 64 | — | — | — | — | — | — | — | — | — |
| Human sarcoma (Ewing's sarcoma) | 52<br>56 | 52<br>56 | 52<br>56 | — | — | — | — | — | — | — |

The apparent molecular weight is given in thousands; n.d. = not determined

From the above results demonstrating that tumor cells carry specific lectins on their surface, the present inventors concluded that lectins and carbohydrates recognizable by lectins which are located on the surface of tumor cells play a key role in the communication between tumor cells as well as between tumor and "normal" cells and furthermore in the process of tissue specific metastasis (homotypic and heterotypic aggregation, see FIG. 1A and B). This provides an experimental basis for lectin impact on growth control and proliferation. If neoplastic cells expose both the lectin and the corresponding carbohydrate and if endogenous lectins can have growth stimulating effects like ConA or PHA, then the tumor cells could stimulate themselves autocatalytically to exponential growth via the lectin-carbohydrate system. This phenomenon may indeed be observed in tumor colonies in vitro and in vivo. Of course, only the two together, the glycoconjugate and its lectin, make sense in biological function.

From the above conclusions of the inventors it can be taken that in contrast to conventional tumor markers, the endogenous lectins are functional tumor markers, which participate in processes of tumor growth and spread.

Therefore, the lectin pattern of a tumor in principle can be characteristic for the type of tumor as compared with the nontransformed cell type, the developmental stage or degree of differentiation of the particular tumor, the tissue environment of the particular tumor.

Thus, the results of the experiments of the present invention permit the conception of new compositions useful for diagnosis and therapy of said tumors and also of functional tests to detect tumor cells at early stages of malignancy.

The diagnostic compositions of the present invention are based on the principle that either the tumor cell specific lectin(s) is (are) detected by the corresponding carbohydrate(s) or by corresponding monoclonal antibodies or antibody-subfragments or the tumor cell specific carbohydrate(s) is (are) detected by the corresponding lectin(s). For the purpose of suitable assays either the lectin(s), the carbohydrate(s), the monoclonal antibodies or the antibody-subfragments are conjugated with a biologically active compound or a compound permitting the detection of the respective molecules in said assay or alternatively the carbohydrates are radioactively labelled. Examples of useful markers or labels are enzymes, fluorochromes or spin labels. It is obvious to a person skilled in the art that immunological assays such as RIA (radioimmunoassay) or ELISA (enzyme-linked immunosorbent assay) may be carried out by using the respective monoclonal antilectin-antibodies or their subfragments.

Advantageously the diagnostic compositions of this invention permit a rapid, reliable, and precise analysis of tumor cells and are therefore inter alia useful for the determination of malignancy of tumors during surgical treatments, for differential diagnosis to distinguish tumor types, and for the determination of the developmental stage of a tumor.

As to the pharmaceutical compositions, as yet the difficult objective in the chemotherapy of cancer and certain other diseases was the lacking selectiveness of the applicated drugs.

A main feature of the pharmaceutical compositions of the present invention is the highly specific interaction of lectins and carbohydrates on the one hand and of lectins and monoclonal antibodies or their subfragments on the other hand. For better understanding the revolutionary effectiveness of said therapeutic compositions some examples are given in the following.

If chemotherapeutic (e.g. methotrexate) or biologically active substances (e.g. a subunit of the cholera toxin) are conjugated with lectin(s) or with suitable carbohydrate(s) or with monoclonal anti-lectin-antibodies or subfragments thereof (i.e. synthesis of immunotoxins), they can be specifically targeted to tumor cells carrying the specific carbohydrates or the specific lectins. The specific action of the drug on tumor cells and only on these excludes essentially the side reactions of classical chemotherapeutic agents.

Furthermore the metastasis of tumors can be inhibited by oral or intravenous administration of suitable carbohydrates in such amounts that a complex or complexes with their corresponding lectin(s) are formed. Thus, they are blocking the binding site for adhesion between tumor cell and cells of the target organ.

Figure 1A:
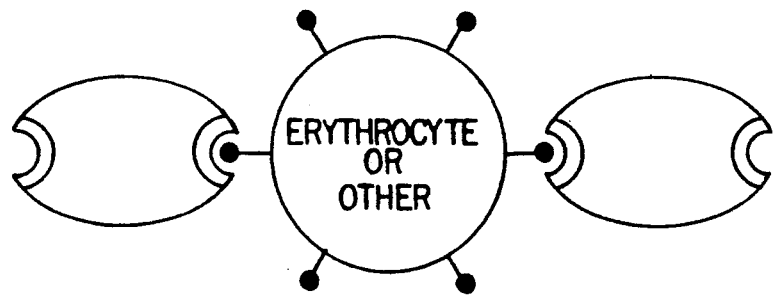
FIG. 1(a) shows a model for heterotypic cell aggregation via the glycoconjugate-lectin system.
Figure 1B:
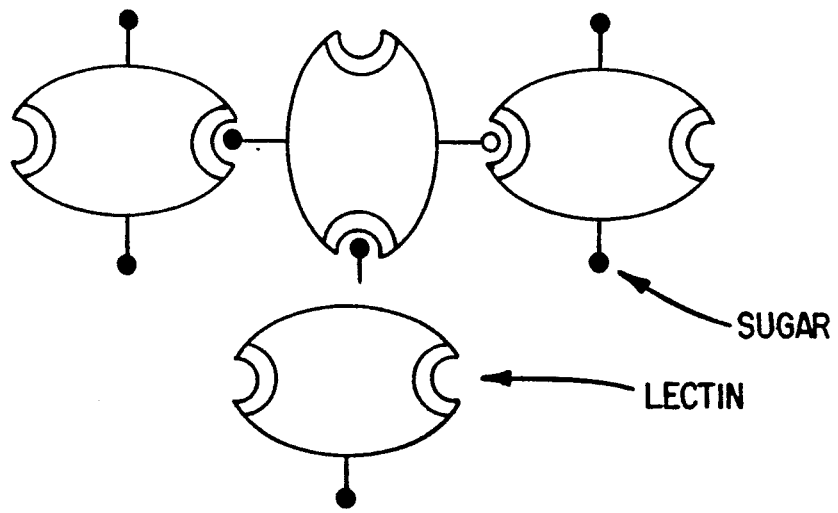
FIG. 1(b) shows a model for homotypic cell aggregation via the glycoconjugate-lectin system.

The following examples further illustrate the invention.

EXAMPLE 1

Isolation and Characterization of Lectins Derived From Mammalian Tumor Cells

The pattern under investigation includes specificities for α- and β-galactosides, α-mannosyl and α-fucosyl residues. It is divided into categories for dependence of the binding activity on the presence of $Ca^{2+}$ and on the extraction conditions, representing soluble intra- and extracellular proteins and integral membrane proteins.

Typically, acetone powder from frozen and thawed tumor tissue (50 g) was prepared by two successive extractions with 6 volumes of −70° C. acetone in a Waring Blendor. The resulting 21 g of powder was extracted twice with 120 ml Buffer A (0.02M Tris/HCl, pH 7.8, containing 0.2M NaCl, 1 mM dithiothreitol and 0.01 mM phenylmethanesulfonylfluoride). The supernatants were combined and brought to a final concentration of 0.5% Triton X-100, 25 mM $CaCl_2$ and 1.25M NaCl. The residual pellet was extracted twice with 120 ml of Buffer B (0.02M Tris/HCl, pH 7.8, containing 0.4M KCl, 2% Triton X-100, 1 mM dithiothreitol and 0.01 mM phenylmethanesulfonyl fluoride), the extracts were combined and adjusted to a concentration of 25 mM $CaCl_2$. Both solutions were separately passed over a set of five columns (0.9×11 cm lactose-, asialo-fetuin-, melibiose- and mannan-Sepharose 4 B, 0.5×10 cm fucose-Sepharose 4 B) equilibrated with Buffer C (0.02M Tris/HCl, pH 7.8, containing 1.25M NaCl, 25 mM $CaCl_2$, 0.05% Triton X-100 and 1 mM dithiothreitol). The column resins (lactose-, asialofetuin-, melibiose-, mannose- and fucose-Sepharose 4 B, using Sepharose 4 B from Pharmacia, Freiburg, FRG and carbohydrates from Sigma, Munich, FRG) had been prepared after suitable activation (divinyl sulphone, cyanogen bromide from Merck, Darmstadt, FRG) according to standard procedures. Also reductive amination of disaccharides to an amino ethylated polyacrylamide support is possible. Asialo-fetuin was prepared from fetuin (Sigma, Munich, FRG) by desialylation at pH 2 and 80° C. After extensive washing of the columns, elution of the $Ca^{2\oplus}$-dependent carbohydrate-binding proteins from the salt extract and the detergent extract was performed using Buffer D (Buffer C containing 4 mM EDTA instead of 25 mM $CaCl_2$).

The material was pooled, readjusted to 25 mM $CaCl_2$ and adsorbed to a smaller column of the corresponding resin (3 ml volume). As was noted before, it is advantageous to perform the second elution with the specific sugars (0.5M lactose, 0.5M melibiose, 0.5M D-mannose, 0.5M L-fucose). In general, elution with a molarity of 0.3 has proved sufficient for complete elution of lectins. The $Ca^{2+}$-independent carbohydrate-binding proteins were eluted by application of Buffer C+0.5M of the specific sugar from the first set of columns that had been reequilibrated with Buffer C. The sugar was removed by dialysis, and affinity chromatography was repeated on small columns (3 ml).

Specificity at this stage was checked by unsuccessful binding of lectins in the presence of specific sugars (0.3M) and by in vitro binding to cytochemical markers on nitrocellulose (Gabius et al., J. Natl. Cancer Inst. 73 (1984), p. 1349). Furthermore, bound lectins were not elutable by unspecific sugars like sucrose.

This procedure allowed the separation of $Ca^{2+}$-dependent lectins from $Ca^{2+}$-independent lectins. In this example five carbohydrate specificities were tested. Of course, many other specificities can be tested in the same way, such as specificities for neuraminic acid, rhamnose, heparin, galactosamine, glucosamine and methylated and acetylated derivatives of these carbohydrates.

The samples were concentrated by ultrafiltration using a membrane as filter (YM5 filter, Amicon). All lectins were characterized with respect to homogeneity and molecular weight by polyacrylamide gel electrophoresis in the presence of 0.1% sodium dodecyl sulfate on 20×20 cm 10% running gels with a 3% stacking gel. The gels were stained with Coomassie blue for heparin-inhibitable lectin or by the silver staining method according to Morrissey (Anal. Biochem. 117 (1981), p. 307) for all other samples.

Standards for molecular weight designation were: phosphorylase b (97 kDa), bovine serum albumin (66 kDa), egg albumin (44 kDa), glyceraldehyde-3-phosphate dehydrogenase (36 kDa), carbonic anhydrase (29 kDa), trypsinogen (24 kDa), and β-lactoglobin (18.4 kDa).

Furthermore the lectins were optionally characterized by hemagglutination, enzyme and aggregation assays. Lectin activity was assayed in microtiter plates with V-shaped bottoms with glutaraldehyde-fixed, trypsin-treated rabbit erythrocytes that in the case of heparin-inhibitable lectin were pretreated with ethanol. All agglutination assays were scored after 1 h at room temperature.

Enzyme assays for β-galactosidase, sialyltransferase and fucosyltransferase, using asialofetuin as potential acceptor, α-mannosidase and α-fucosidase were performed.

The sensitivity of the assay varied from a detection limit of $1.5\times10^{-8}$ unit of enzyme activity for transferases to $5\times10^{-4}$ unit of enzyme for glycosidases (1 unit = μmol of substrate converted per min). Aggregation of cerebroside vesicles (12 mol % N-plamitoyl-DL-dihydrolactocerebroside) by β-galactoside specific lectins was performed at a concentration of 7 μg/ml lectin.

With each isolation procedure identical results were achieved at least twice.

EXAMPLE 2

Isolation and Characterization of Lectins Derived From a Spontaneous Rat Rhabdomyosarcoma, a Rat Fibroadenoma, Two Rat Tubulopapillary Adenocarcinomas and a Murine Teratoma Basically according to the procedure described in Example 1 five different tumor types were investigated biochemically for the presence and characteristics of endogenous carbohydrate-binding proteins (lectins).

The tumors had developed spontaneously in female rats or mice which were obtained from the breeding colonies of the Central Institute for Laboratory Animal Breeding, Lettow-Vorbeck-Allee 57, 3000 Hannover 91, West Germany.

The rat rhabdomyosarcoma originated from the thoracic cavity of an inbred Brown Norway rat (BN/Han) and was attached to the cranioventral section of the sternum and the ribs. The second tumor, a fibroadenoma of the mammary gland, was found in a 9 months old female breeder rat of the Han: SPRD outbred stock which was removed from the breeding colony of the institute for routine hygienic monitoring. The third and the fourth tumors can both be classified as belonging to the tubulopapillary adenocarcinoma group. The third tumor, an invasive tubulopapillary adenocarcinoma, had developed in the inguinal area of an outbred Sprague-Dawley rat (Han: SPRD) and was observed in a life-span study maintaining rats from weaning up to their natural deaths. The fourth tumor, a non-invasive rat tubulopapillary adenocarcinoma displayed a higher degree of differentiation than the third tumor and was obtained from an inbred BDII/Han rat.

The murine teratoma developed in a 6 months old Han:NMRI mouse in the left ovary. This mouse teratoma was well differentiated, consisting of various tissues as bone, cartilage, connective tissue, striated and smooth muscle cells, nervous tissue including retina, and an epithelial component.

The purification and characterization of lectins started from 6 g of a rat rhabdomyosarcoma, 22.7 g of a rat fibroadenoma, 27 g of an invasive rat tubulopapillary adenocarcinoma, 15.5 g of a non-invasive tubulopapillary adenocarcinoma and 28 g of a murine teratoma.

The rat rhabdomyosarcoma was homogenized in 6 volumes of extraction medium (75 mM $Na_2HPO_4$/$KH_2PO_4$, pH 7.2, 75 mM NaCl, 4 mM β-mercaptoethanol, 2 mM EDTA and 0.01 mM phenylmethanesulfonyl fluoride (MEPBS) containing 1M NaCl, 0.2M lactose and 0.2M mannose). After centrifugation and dialysis first against MEPBS, later against a buffer with Tris-HCl (75 mM) instead of phosphate, raised successively from pH 7.5 to pH 7.8, the solution was adjusted to 20 mM $CaCl_2$ and successively passed over a set of columns (0.9 × 12 cm) equilibrated with buffer A (75 mM Tris-HCl, pH 7.8, 25 mM $CaCl_2$, 4 mM β-mercaptoethanol, 2 mM EDTA, 0.01 mM phenylmethane-sulfonyl fluoride and 1M NaCl). The columns were processed as in Example 1. The extract, after passing over the columns, was concentrated, submitted to a column chromatography with Sepharose CL-2B (Pharmacia, Freiburg, FRG) and dialyzed in the presence of 40 ml heparin-Sepharose 4B against 0,01M Tris-HCl, pH 8.6, 4 mM β-mercaptoethanol and 0.3M NaCl. Elution from the columns was performed by two means:

a) with buffer A after omission of $CaCl_2$ and addition of 4 mM EDTA, b) after reequilibration with buffer A using buffer A+0.5M of the appropriate sugar (lactose, melibiose, mannose, fucose).

After dialysis of the samples against buffer A, the affinity chromatography for analysing the lectin pattern was repeated using columns with a capacity of 5 ml.

The lectin pattern of the other tumors was analysed exactly as described in Example 1.

Furthermore, the lectins isolated from said rat and mouse tumors were subjected to characterization by gel electrophoresis, hemagglutination assays, and enzymatic assays as described in Example 1.

The lectins which were obtained and which were not known from any type of normal mammalian tissue are given in Table I.

EXAMPLE 3

Isolation and Characterization of Lectins Derived From a Human Malignant Epithelial Tumor The tumor was surgically removed from the left flexura of the colon of a 60 year old woman.

The preparation of the lectins from the tumor tissue was carried out as described in Example 1 starting with 34 g frozen and thawed tumor material.

The preparation was carried out three times with identical results.

Subsequently the lectins of this epithelial tumor were further characterized by demonstrating hemagglutinating activity and excluding any detectable enzymatic activity according to the methods given in Example 1.

The lectins obtained from this human epithelial tumor which were not known from any type of normal mammalian tissue are summarized in Table I.

EXAMPLE 4

Isolation and Characterization of Lectins Derived From Different Human Testicular Tumors Essentially according to the procedure given in Example 1 the lectin pattern of a human teratocarcinoma was analyzed.

The teratocarcinoma cell line H12.1 had been established from a primary human testis tumor and was subcultured more than 60 times in vitro. The culture was maintained in RPMI 1640 medium (Flow Labs, Meckenheim, FRG) containing 15% heat inactivated fetal calf serum (Biochrom, Berlin, FRG), 10% tryptose phosphate broth (Flow Labs, Meckenheim, FRG), 2 mM L-glutamin, 100 I.U./ml penicillin and 100 μg/ml streptomycin. For transplantation athymic nude NMRI mice (nu/nu, 6–8 weeks old) were treated subcutaneously with approximately $10^7$ cells. After 2 months the tumors were removed, immediately frozen in liquid nitrogen and stored at −80° C. For the preparation of lectin from the culture, cells were washed with buffer (75 mM Tris/HCl, pH 7.8, containing 1 mM phenylmethanesulfonyl fluoride, 2 mM dithiothreitol and 1 mM $NaN_3$), scraped out and frozen. Homogenization of 1 g cells (wet weight) was carried out with the same buffer containing 2% Triton X-100 and lacking $NaN_3$.

In a typical preparation of lectins, acetone powder of tumor material (14 g) was extracted and fractionated as given in Example 1.

All samples after two cycles of affinity chromatography were concentrated by ultrafiltration using a membrane as filter (Diaflo Ultrafiltration Model 50 with a YM-5 membrane). Detergent was removed by chloroform extraction and the heparin-specific lectin was isolated from the tumor material. Subsequently, the lectin pattern was analysed according to Example 1, including tests for hemagglutinating and enzyme activity.

To demonstrate the possible functional role of the lectins of said human teratocarcinoma cells, the binding of erythrocytes to these teratocarcinoma cells was monitored in a simple visual assay using trypsinized, glutaraldehyde-fixed rabbit erythrocytes (rosette formation). Since carbohydrate structures on the surface of erythrocytes apparently are recognized by carbohydrate-binding proteins of the teratocarcinoma cells during the heterotypic recognition, inhibition of this process by addition of sugars and glycoproteins was tested (Table II).

TABLE II

| Inhibitor | Inhibition of rosette formation<br>% Inhibition of rosette formation |
|---|---|
| N-acetyl-D-galactosamine | 0 |
| L-fucose | 2 |
| D-galactose | 4 |
| N-acetyl-D-glucosamine | 0 |
| D-mannose | 10 |
| fetuin | 0 |
| asialofetuin | 7 |
| asialo-agalactofetuin | 0 |
| mannan | 21 |
| Invertase | 34 |
| Invertase (periodate-oxidized) | 4 |
| lactose-BSA | 7 |
| mannose-BSA | 14 |

Saccharides were added at 0.2M, glycoproteins at 1 mg/ml. All results are averages from 8-10 independent experiments.

Whereas monosaccharides as D-mannose and D-galactose only slightly inhibited the heterotypic aggregation at 0.2M concentration, a more pronounced effect was seen with glycosylated bovine serum albumin (lac-BSA, man-BSA). Since galactose-binding proteins were known to bind to the mannose-glycoprotein invertase, the difference in inhibitory efficiency of invertase in relation to mannan may indicate a binding of invertase to galactose- and mannose-specific sites on the teratocarcinoma cells. No inhibition was seen with N-acetyl-glucosamine, asialoagalactofetuin, fetuin, glucose and sucrose. This excludes an unspecific sugar effect on rosette formation. Bovine serum albumin (BSA) also had no inhibitory influence. Coupling of p-aminophenyl-glucoside by diazotation to BSA, as similarly used for the derivatives of β-lactose and α-D-mannose, does not influence the inertness of BSA in rosette formation, excluding any uspecific effect due to the chemical modification procedure. Since the inhibition by invertase is drastically reduced after extensive oxidation of sugar moieties in invertase by periodate treatment, the importance of sugars in the recognitive process during rosette formation is further emphasized.

Figure 2A:
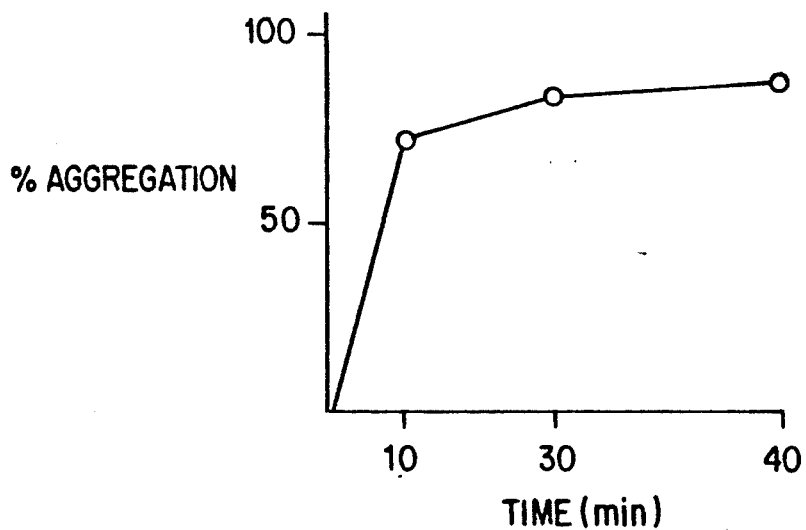
FIGS. 2(a) and 2(b) show the inhibition of homotypic human teratocarcinoma cell aggregation by sugars. The aggregation in the absence of the inhibitor is given in 2(a), the aggregation in the presence of varying concentrations of L-fucose (o), D-galactose (x) and D-mannose (+) after 15 minutes is given in 2(b).
Figure 2B:
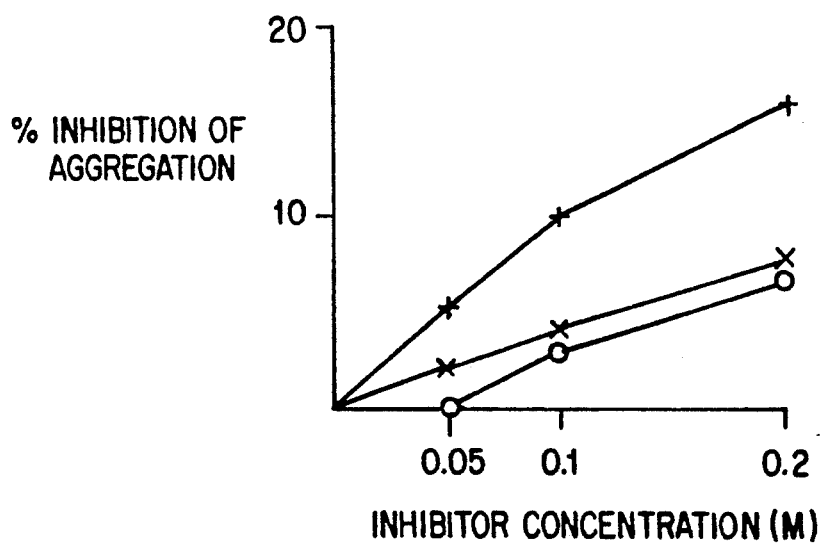

Inhibition of rosette formation carried out as described above demonstrated the participation of a protein carbohydrate interaction in heterotypic aggregation. Since type and abundancy of carbohydrate structures of glycoconjugates on erythrocytes and teratocarcinoma cells might differ significantly, the influence of sugars on reaggregation of teratocarcinoma cells that were carefully mechanically dissociated in calcium-and magnesium-free phosphate-buffered saline was tested. The tests revealed a similar inhibition pattern for the homotypic aggregation in relation to the heterotypic system, with mannose and galactose being effective inhibitors (FIGS. 2(a) and 2(b)). The ability of D-mannose and D-galactose to inhibit aggregation of teratocarcinoma cells further suggested that these sugars interact with cell surface carbohydrate-binding proteins. In order to establish the capacity of sugars to bind to carbohydrate-binding proteins of the cell surface, fluorescent, glycosylated markers provided a versatile cytological tool for visualization. Observation of teratocarcinoma cells after labelling with markers specific for D-mannose and lactose resulted in significant binding of markers. The binding was performed at 4° C. in order to minimize internalization or shedding of membrane-bound proteins. Complete inhibition of binding occurred in the presence of the appropriate sugar (D-mannose or lactose) in a 0.25M concentration or of 1 mg/ml unlabelled glycosylated BSA. These data provided evidence that the lectins contained in the detergent extract of human teratocarcinoma cells being specific for D-mannose and D-galactose are involved in $Ca^{2+}$-independent cell-cell recognition.

The human embryonic carcinoma cell line H 23 had been established from a primary human testicular tumor of a 26 year old patient and was subcultured more than 30 times in vitro. For transplantation, athymic nude mice (nu/nu, 6–8 weeks old) (Central Institute for Animal Breeding, supra) were injected subcutaneously with approximately $10^7$ cells. After two months the tumors, histologically determined as embryonic carcinoma, were removed, immediately frozen in liquid nitrogen and stored at −80° C.

The yolk sac tumor material was obtained by autopsy of a 20 year old boy suffering from a testicular embryonic carcinoma. Viable parts of the abdominal tumor mass were removed, consisting histologically predominantly of yolk sac tumor material.

The lectins of said human embryonic carcinoma cell line H 23 and of said yolk sac tumor were isolated and characterized according to Example 1, including functional tests for hemagglutinating and enzyme activity.

The lectins identified in the above-mentioned human testicular tumors which were not known from any type of normal mammalian tissue are summarized in Table I.

The analyzed lectin patterns demonstrate that lectins can be considered as functional tumor markers useful for differential diagnosis of tumors and different developmental stages of tumors.

EXAMPLE 5

Isolation and Characterization of Lectins Derived From a Rat Osteosarcoma and a Human Sarcoma (Ewing's Sarcoma)

The lectin pattern of a rat osteosarcoma was determined by analysis of 3 g tumor tissue as described in Example 1.

Tumor material of the human sarcoma (Ewing's sarcoma) was obtained from the Cancer Center of the University of California, San Diego. 3.5 of the tissue were extracted and analyzed for their lectin pattern as described in Example 1.

Subsequently, functional tests for hemagglutinating and enzyme activity were carried out according to Example 1.

The lectins obtained from these tumors which were not known from any type of normal mammalian tissue are summarized in Table I.

We claim:

1. Purified carbohydrate-binding proteins isolated from a mammalian tumor cell and which only occur on the surface of the tumor cell and not on the surface of a corresponding normal cell, said proteins consisting of lectins having the following characteristics:
   (a) the recognition of carbohydrates is highly specific and comparable to the antigen-specificity of antibodies or the substrate-specificity of enzymes;
   (b) the lectins are of non-immune origin, in contrast to antibodies;
   (c) the lectins do not display any detectable enzymatic activity, in contrast to enzymes; and
   (d) the lectins display homotypic and heterotypic agglutinating activity that is inhibited by only the carbohydrates to which they selectively bind.

2. Purified carbohydrate-binding proteins isolated from a mammalian tumor cell and which are functional tumor markers of said tumor cell and which participate in processes of growth and spread of said tumor cell, said proteins consisting of lectins having the following characteristics:
   (a) the recognition of carbohydrates is highly specific and comparable to the antigen-specificity of antibodies or the substrate-specificity of enzymes;
   (b) the lectins are of non-immune origin, in contrast to antibodies;
   (c) the lectins do not display any detectable enzymatic activity, in contrast to enzymes;
   (d) the lectins display homotypic and heterotypic agglutinating activity that is inhibited by only the carbohydrates to which they selectively bind; and
   (e) the lectins are not present in a corresponding normal cell.

3. A purified tumor-specific lectin composition obtained from a mammalian tumor by performing the following steps in order:
   a) extracting tissue of the tumor with acetone to precipitate proteins in the tumor;
   b) evaporating the acetone to obtain a powder;
   c) extracting the powder from step (b) with a buffered aqueous solution for solubilizing the proteins;
   d) adsorbing carbohydrate-specific proteins contained in the aqueous extract to suitable respective carbohydrates bound to an affinity chromatographic column;
   e) eluting calcium ion-dependent proteins from the column with an aqueous solution of a chelating agent;
   f) eluting calcium ion-independent proteins from the column with an aqueous solution of a carbohydrate;
   g) performing hemagglutination, enzyme activity, and aggregation assays of the eluted proteins from steps e) and f) to characterize the eluted proteins as lectins having no detectable enzyme activity and which are of non-immune origin.

4. A purified tumor-specific lectin composition according to claim 3 wherein the buffered aqueous solution of step c) comprises a neutral buffer base, pH about 7.8, containing 0.2M NaCl.

5. A purified tumor-specific lectin composition according to claim 3 wherein the buffered aqueous solution of step c) further comprises a neutral buffer base, pH about 7.8, containing 0.4M KCl and 2% nonionic detergent.

6. A purified tumor-specific lectin composition according to claim 3 wherein the bound carbohydrates of the column in step d) are selected from the group consisting of lactose, asialofetuin, melibiose, mannan, fucose, neuramic acid, rhamnose, heparin, galactosamine, glucosamine, and methylated and acetylated derivatives of these carbohydrates.

7. A purified tumor-specific lectin composition according to claim 3 wherein the tumor is a rat rhabdomyosarcoma, and the composition comprises:
   (a) calcium-independent malibiose-binding lectin having molecular weights of 29, 43, and 45 kilodaltons;
   (b) calcium-independent mannan-binding lectins having molecular weights ranging from 60 to 72 kilodaltons; and
   (c) calcium-independent fucose-binding lectins having molecular weights ranging from 60 to 72 kilodaltons.

8. A purified tumor-specific lectin composition according to claim 3 wherein the tumor is a rat fibroadenoma, and the composition comprises:
   a) calcium-dependent lactose-binding lectins having molecular weights of 52, 67, and 130 kilodaltons;
   b) calcium-dependent asialofetuin-binding lectins having molecular weights of 52, 67, and 130 kilodaltons;
   c) calcium-dependent melibiose-binding lectins having molecular weights of 52, 67, and 74 kilodaltons;
   d) calcium-dependent mannan-binding lectins having molecular weights of 52 and 67 kilodaltons; and
   e) calcium-dependent fucose-binding lectins having molecular weights of 29 and 67 kilodaltons.

9. A purified tumor-specific lectin composition according to claim 3 wherein the tumor is a rat invasive tubulopapillary adenocarcinoma with a low degree of differentiation, and the composition comprises:
   a) calcium-dependent lactose-binding lectins having molecular weights of 32 and 64 kilodaltons;
   b) calcium-dependent fucose-binding lectin having a molecular weight of 140 kilodaltons;
   c) calcium-independent lactose-binding lectins having molecular weights of 22 and 52 kilodaltons;
   d) calcium-independent mannan-binding lectins having molecular weights of 44 and 46 kilodaltons; and
   e) calcium-independent fucose-binding lectins having molecular weights of 13, 30, 42, 45, and 62 kilodaltons.

10. A purified tumor-specific lectin composition according to claim 3 wherein the tumor is a rat non-invasive tubulopapillary adenocarcinoma with a high degree of differentiation, and the composition comprises:
    a) calcium-dependent fucose-binding lectins having molecular weights of 29 and 35 kilodaltons;
    b) calcium-independent melibiose-binding lectins having molecular weights of 29, 50, and 52 kilodaltons; and
    c) calcium-independent fucose-binding lectins having molecular weights of 29, 31, 50, and 52 kilodaltons.

11. A purified tumor-specific lectin composition according to claim 3 wherein the tumor is a murine teratoma, and the composition comprises:
    a) calcium-dependent lactose-binding lectin having a molecular weight of 24 kilodaltons;

b) calcium-dependent mannan-binding lectin having a molecular weight of 32 kilodaltons;

c) calcium-dependent fucose-binding lectin having a molecular weight of 32 kilodaltons; and d) calcium-independent fucose-binding lectin having a molecular weight of 100 kilodaltons.

12. A purified tumor-specific lectin composition according to claim 3 wherein the tumor is a human malignant epithelial tumor, and the composition comprises:

a) calcium-dependent lactose-binding lectin having a molecular weight of 70 kilodaltons;

b) calcium-dependent melibiose-binding lectins having molecular weights of 28, 43, and 45 kilodaltons;

c) calcium-dependent fucose-binding lectins having molecular weights of 62 and 70 kilodaltons;

d) calcium-independent melibiose-binding lectin having a molecular weight of 64 kilodaltons; and e) calcium-independent fucose-binding lectin having a molecular weight of 62 kilodaltons.

13. A purified tumor-specific lectin composition according to claim 3 wherein the tumor is a human teratocarcinoma, and the composition comprises:

a) calcium-dependent melibiose-binding lectin having a molecular weight of 31 kilodaltons;

b) calcium-dependent fucose-binding lectins having molecular weights of 31 and 70 kilodaltons; and c) calcium-independent mannan-binding lectin having a molecular weight of 68 kilodaltons.

14. A purified tumor-specific lectin composition according to claim 3 wherein the tumor is a human embryonic carcinoma, and the composition comprises:

a) calcium-dependent melibiose-binding lectins having molecular weights of 56 and 66 kilodaltons;

b) calcium-dependent mannan-binding lectin having a molecular weight of 66 kilodaltons;

c) calcium-dependent fucose-binding lectin having a molecular weight of 31 kilodaltons; and d) calcium-independent lactose-binding lectin having a molecular weight of 32 kilodaltons.

15. A purified tumor-specific lectin composition according to claim 3 wherein the tumor is a human yolk sac carcinoma, and the composition comprises:

(a) calcium-dependent lactose-binding lectin having a molecular weight of 56 kilodaltons;

(b) calcium-dependent melibiose-binding lectin having a molecular weight of 56 kilodaltons;

(c) calcium-dependent fucose-binding lectins having molecular weight of 29 and 56 kilodaltons;

(d) calcium-independent lactose-binding lectins having molecular weight of 29 and 56 kilodaltons;

(e) calcium-independent asialofetuin-binding lectins having molecular weight of 29 and 56 kilodaltons;

(f) calcium-independent melibiose-binding lectins having molecular weights of 29 and 56 kilodaltons; and (g) calcium-independent fucose-binding lectins having molecular weights of 29, 56, and 62 kilodaltons.

16. A purified tumor-specific lectin composition according to claim 3 wherein the tumor is a rat osteosarcoma, and the composition comprises a calcium-dependent lactose-binding lectin having a molecular weight of 64 kilodaltons.

17. A purified tumor-specific lectin composition according to claim 3 wherein the tumor is a human sarcoma (Ewing's sarcoma), and the composition comprises:

a) calcium-dependent lactose-binding lectins having molecular weights of 52 and 56 kilodaltons;

b) calcium-dependent asialofetuin-binding lectins having molecular weights of 52 and 56 kilodaltons; and c) calcium-dependent melibiose-binding lectins having molecular weights of 52 and 56 kilodaltons.

18. Purified carbohydrate-binding proteins that are responsible for cancer-specific properties of a tumor cell, isolated from a mammalian tumor cell selected from the group consisting of rat rhabdomyosarcoma, rat fibroadenoma, rat invasive tubulopapillary adenocarcinoma with a low degree of differentiation, rat noninvasive tubulopapillary adenocarcinoma with a high degree of differentiation, murine teratoma, human malignant epithelial tumor, human teratocarcinoma, human embryonic carcinoma, human yolk sac carcinoma, rat osteosarcoma, and human sarcoma (Ewing's sarcoma), said proteins consisting of lectins having the following characteristics:

(a) each lectin binds to only a specific carbohydrate selected from the group consisting of lactose, asialofetuin, melibiose, mannan, fucose, neuramic acid, rhamnose, heparin, galactosamine, glucosamine, and methylated and acetylated derivatives of these carbohydrates;

(b) the lectins are not antibodies;

(c) the lectins are not enzymes;

(d) the lectins display homotypic and heterotypic agglutinating activity that is inhibited by only the carbohydrates to which they selectively bind; and (e) the lectins are tumor-specific to the same tumor from which the lectin is isolated and are not present in any type of normal mammalian cell.

19. A purified tumor-specific lectin composition according to claim 18 wherein the tumor is a rat rhabdomyosarcoma, and the composition comprises:

(a) calcium-independent melibiose-binding lectins having molecular weights of 29, 43, and 45 kilodaltons;

(b) calcium-independent mannan-binding lectins having molecular weights ranging from 60 to 72 kilodaltons; and (c) calcium-independent fucose-binding lectins having molecular weights ranging from 60 to 72 kilodaltons.

20. A purified tumor-specific lectin composition according to claim 18 wherein the tumor is a rat fibroadenoma, and the composition comprises:

a) calcium-dependent lactose-binding lectins having molecular weights of 52, 67, and 130 kilodaltons;

b) calcium-dependent asialofetuin-binding lectins having molecular weights of 52, 67, and 130 kilodaltons;

c) calcium-dependent melibiose-binding lectins having molecular weights of 52, 67, and 74 kilodaltons;

d) calcium-dependent mannan-binding lectins having molecular weights of 52 and 67 kilodaltons; and e) calcium-dependent fucose-binding lectins having molecular weights of 29 and 67 kilodaltons.

21. A purified tumor-specific lectin composition according to claim 18 wherein the tumor is a rat invasive tubulopapillary adenocarcinoma with a low degree of differentiation, and the composition comprises:

a) calcium-dependent lactose-binding lectins having molecular weights of 32 and 64 kilodaltons;

b) calcium-dependent fucose-binding lectin having a molecular weight of 140 kilodaltons;

c) calcium-independent lactose-binding lectins having molecular weights of 22 and 52 kilodaltons;

d) calcium-independent mannan-binding lectins having molecular weights of 44 and 46 kilodaltons; and
e) calcium-independent fucose-binding lectins having molecular weights of 13, 30, 42, 45, and 62 kilodaltons.

22. A purified tumor-specific lectin composition according to claim 18 wherein the tumor is a rat non-invasive tubulopapillary adenocarcinoma with a high degree of differentiation, and the composition comprises:
a) calcium-dependent fucose-binding lectins having molecular weights of 29 and 35 kilodaltons;
b) calcium-independent melibiose-binding lectins having molecular weights of 29, 50, and 52 kilodaltons; and
c) calcium-independent fucose-binding lectins having molecular weights of 29, 31, 50, and 52 kilodaltons.

23. A purified tumor-specific lectin composition according to claim 18 wherein the tumor is a murine teratoma, and the composition comprises:
a) calcium-dependent lactose-binding lectin having a molecular weight of 24 kilodaltons;
b) calcium-dependent mannan-binding lectin having a molecular weight of 32 kilodaltons;
c) calcium-dependent fucose-binding lectin having a molecular weight of 32 kilodaltons; and
d) calcium-independent fucose-binding lectin having a molecular weight of 100 kilodaltons.

24. A purified tumor-specific lectin composition according to claim 18 wherein the tumor is a human malignant epithelial tumor, and the composition comprises:
a) calcium-dependent lactose-binding lectin having a molecular weight of 70 kilodaltons;
b) calcium-dependent melibiose-binding lectins having molecular weights of 28, 43, and 45 kilodaltons;
c) calcium-dependent fucose-binding lectins having molecular weights of 62 and 70 kilodaltons;
d) calcium-independent melibiose-binding lectin having a molecular weight of 64 kilodaltons; and
e) calcium-independent fucose-binding lectin having a molecular weight of 62 kilodaltons.

25. A purified tumor-specific lectin composition according to claim 18 wherein the tumor is a human teratocarcinoma, and the composition comprises:
a) calcium-dependent melibiose-binding lectin having a molecular weight of 31 kilodaltons;
b) calcium-dependent fucose-binding lectins having molecular weights of 31 and 70 kilodaltons; and
c) calcium-independent mannan-binding lectin having a molecular weight of 68 kilodaltons.

26. A purified tumor-specific lectin composition according to claim 18 wherein the tumor is a human embryonic carcinoma, and the composition comprises:
a) calcium-dependent melibiose-binding lectins having molecular weights of 56 and 66 kilodaltons;
b) calcium-dependent mannan-binding lectin having a molecular weight of 66 kilodaltons;
c) calcium-dependent fucose-binding lectin having a molecular weight of 31 kilodaltons; and
d) calcium-independent lactose-binding lectin having a molecular weight of 32 kilodaltons.

27. A purified tumor-specific lectin composition according to claim 18 wherein the tumor is a human yolk sac carcinoma, and the composition comprises:
(a) calcium-dependent lactose-binding lectin having a molecular weight of 56 kilodaltons;
(b) calcium-dependent melibiose-binding lectin having a molecular weight of 56 kilodaltons;
(c) calcium-dependent fucose-binding lectins having molecular weights of 29 and 56 kilodaltons;
(d) calcium-independent lactose-binding lectins having molecular weights of 29 and 56 kilodaltons;
(e) calcium-independent asialofetuin-binding lectins having molecular weights of 29 and 56 kilodaltons;
(f) calcium-independent melibiose-binding lectins having molecular weights of 29 and 56 kilodaltons; and
(g) calcium-independent fucose-binding lectins having molecular weights of 29, 56, and 62 kilodaltons.

28. A purified tumor-specific lectin composition according to claim 18 wherein the tumor is a rat osteosarcoma, and the composition comprises a calcium-dependent lactose-binding lectin having a molecular weight of 64 kilodaltons.

29. A purified tumor-specific lectin composition according to claim 18 wherein the tumor is a human sarcoma (Ewing's sarcoma), and the composition comprises:
a) calcium-dependent lactose-binding lectins having molecular weights of 52 and 56 kilodaltons;
b) calcium-dependent asialofetuin-binding lectins having molecular weigths of 52 and 56 kilodaltons; and
c) calcium-dependent melibiose-binding lectins having molecular weights of 52 and 56 kilodaltons.

* * * * *

UNITED STATES PATENT AND TRADEMARK OFFICE
CERTIFICATE OF CORRECTION

PATENT NO. : 5,225,542
DATED : July 6, 1993
INVENTOR(S) : Friedrich Cramer et al It is certified that error appears in the above-indentified patent and that said Letters Patent is hereby corrected as shown below:

Title Page:
    Abstract, line 6 , change "product" to --production--.

Column 2, line 8, after "described." insert --Kawasaki et al.
                            (J. Biochem. 88 (1980), p. 189;--.
Column 2, line 9, after "937" insert --) published--.
Column 4, line 38, change "spontenaous" to --spontaneous--.
Column 6, line 62, change "was the lacking selectiveness" to
                 --has been frustrated by the lack of selectivity--.
Column 6, line 63, change "applicated" to --applied--.
Column 7, line 58, change "asialo-fetuin-," to --asialofetuin-,--.
Column 8, line 3, change "Asialo-fetuin" to --Asialofetuin--.
Column 8, line 6, change "Ca$^{2\oplus}$" to --Ca$^{2+}$--.
Column 12, line 66, after "3.5" insert --g--.

Signed and Sealed this

Fifteenth Day of March, 1994

Attest:

BRUCE LEHMAN

*Attesting Officer*            *Commissioner of Patents and Trademarks*